United States Patent
Rampf et al.

(10) Patent No.: US 6,858,756 B2
(45) Date of Patent: Feb. 22, 2005

(54) ARYLATION OF OLEFINS

(75) Inventors: Florian Rampf, Köln (DE); Markus Eckert, Köln (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/305,877

(22) Filed: Nov. 27, 2002

(65) Prior Publication Data

US 2003/0114707 A1 Jun. 19, 2003

(30) Foreign Application Priority Data

Dec. 3, 2001 (DE) .......................................... 101 59 269

(51) Int. Cl.$^7$ ........................................... C07C 233/00
(52) U.S. Cl. .................................................... 564/182
(58) Field of Search ........................................ 564/182

(56) References Cited

U.S. PATENT DOCUMENTS

| | | | |
|---|---|---|---|
| 3,922,299 A | 11/1975 | Heck ............................ | 260/476 |
| 4,564,479 A | 1/1986 | Spencer ........................ | 260/465 |
| 6,291,383 B1 | 9/2001 | Zapf et al. .................... | 502/103 |

OTHER PUBLICATIONS

Portnoy et al, Organometallics, Reactions of Electron–Rich Arylpalladium Complexes with Olefins. Origin of the Chelate Effect in Vinylation Catalysis, 1994, 13, pp. 3465–3479.*

J. Am. Chem. Soc. (month unavailable) 2001, 123, pp. 6989–7000, Adam F. Littke and Gregory C. Fu, "A Versatile Catalyst for Heck Reactions of Aryl Chlorides and Aryl Bromides under Mild Conditions".

Littke, A F et al: "A versatile catalyst for Heck reactions of aryl chlorides and aryl bromides Under mild conditions" Journal of the American Chemical Society., Bd. 123, Nr. 29, 2001, Seiten 6989–7000 XPOO2236859 American Chemical Society, Washington, DC., US ISSN: 002–7863 Seite 6991, Spalte 12, Zeile 30—Zeile 40 Tabellen 1–3.

Beller M et al: "First Efficient Palladium–Catalyzed Heck Reactions of Aryl Bromides with Alkyl Methacrylate" Tetrahedron Letters, Elsevier Science Publishers, Amsterdam, NL, Bd. 37, Nr. 36, Sep. 2, 1996, Seityen 6535–6538, XPOO4030736 ISSN: 0040–4039 Seite 6536 Beispiele 1 ,4–8; Tabelle 1.

Reetz M T et al: "A New Catalyst System for the Heck Reaction of Unreactive Aryle Halides" Angewandte Chemie. International Edition Verlag Chemie. Weinheim, DE, Bd. 37, Nr. 4, 1998, Seiten 481–483m XPOO2160618, ISSN: 5070–0833 das ganze Dokument.

Baek, G H et al: "Synthesis of 3–Arylpropylamine Derivatives from Aryl Halides Using Heck Reactions" Bulletin of the Korean Chemical Society, XX, XX, Bd. 20, Nr. 2, 1999, Seiten 232–236, XPOO1006391 Seite 232, Spalte 2, Absatz 2 Tab Ile 1.

* cited by examiner

*Primary Examiner*—Paul A. Zucker
(74) *Attorney, Agent, or Firm*—Diderico van Eyl; Godfried R. Akorli

(57) ABSTRACT

The present invention relates to a process for the arylation of olefins by reaction of haloaromatics or arylsulfonates with olefins in the presence of a palladium catalyst, a bulky nitrogen base and a dipolar aprotic solvent.

13 Claims, No Drawings

ARYLATION OF OLEFINS

BACKGROUND OF THE INVENTION

1. Field of the Invention

The present invention relates to a process for the arylation of olefins by reaction of haloaromatics or arylsulfonates with olefins in the presence of a palladium catalyst and a bulky nitrogen base, if appropriate in a dipolar aprotic solvent.

2. Background of the Invention

Many aryl olefins have great industrial importance as fine chemicals, UV absorbers, starting materials for polymers and intermediates for active compounds.

The preparation of arylolefins is frequently carried out by means of palladium-catalyzed coupling of iodoaromatics or bromoaromatics, and to a lesser extent chloroaromatics or arylsulfonates, with olefins. Owing to the high price of iodoaromatics and bromoaromatics and the large amounts of waste product caused by the high molar masses, their use on an industrial scale is disadvantageous. However, the more readily available and therefore more attractive chloroaromatics have a comparatively low reactivity.

Littke and Fu (J. Am. Chem. Soc. 2001, 123, 6989) describe a process in which chloroaromatics are reacted with olefins at room temperature using palladium-dibenzylideneacetone ($[Pd_2(dba)_3]$) and tri-tert-butylphosphine in the presence of dicyclohexylmethylamine in dioxane. However, the turnover numbers (TONs) are low and large amounts of palladium catalyst are required for the process described, which makes its industrial application uneconomical.

There was therefore a need to develop a process which makes it possible for haloaromatics, in particular chloroaromatics, to be coupled with olefins in an efficient way.

SUMMARY OF THE INVENTION

We have now found a process for preparing arylolefins, which is characterized in that aromatic compounds of the general formula (I), $$Ar\text{---}[X]_n \quad (I)$$

where n is one or two and

Ar is a substituted or unsubstituted aromatic radical and

X are each, independently of one another, chlorine, bromine, iodine or a sulphonate, are reacted with olefins which bear at least one hydrogen atom on the double bond in the presence of a palladium catalyst, at least one bulky nitrogen base and in the presence of a dipolar aprotic solvent.

DETAILED DESCRIPTION OF THE INVENTION

It may be pointed out at this juncture that any combinations of preferred ranges are encompassed by the invention.

For the purposes of the invention, Ar is, by way of example and preferably, a carbocyclic aromatic radical having from 6 to 24 framework carbon atoms or a heteroaromatic radical having from 5 to 24 framework carbon atoms in which no, one, two or three framework carbon atom(s) per ring, but at least one framework carbon atom in the total molecule, can be replaced by heteroatoms selected from the group consisting of nitrogen, sulphur and oxygen. Furthermore, the carbocyclic aromatic radicals or heteroaromatic radicals may be substituted by up to five identical or different substituents per ring selected from the group consisting of hydroxy, fluorine, nitro, cyano, free or protected formyl, $C_1$–$C_{12}$-alkyl, $C_5$–$C_{14}$-aryl, $C_6$–$C_{15}$-arylalkyl, —PO—[($C_1$–$C_8$)-alkyl]$_2$, —PO—[($C_5$–$C_{14}$)-aryl]$_2$, —PO—[($C_1$–$C_8$)-alkyl)($C_5$–$C_{14}$)-aryl)], tri($C_1$–$C_8$-alkyl) siloxyl and radicals of the general formula (II), $$A\text{---}B\text{---}D\text{---}E \quad (II)$$

where, independently of one another,

A is absent or is a $C_1$–$C_8$-alkylene radical and

B is absent or is oxygen, sulphur or $NR^1$, where $R^1$ is hydrogen, $C_1$–$C_8$-alkyl, $C_6$–$C_{15}$-arylalkyl or $C_5$–$C_{14}$-aryl and D is a carbonyl group and E is $R^2$, $OR^2$, $NHR^3$ or $N(R^3)_2$, where $R^2$ is $C_1$–$C_8$-alkyl, $C_6$–$C_{15}$-arylalkyl, $C_1$–$C_8$-haloalkyl or $C_5$–$C_{14}$-aryl and $R^3$ are each, independently of one another, $C_1$–$C_8$-alkyl, $C_6$–$C_{15}$-arylalkyl or $C_6$–$C_{14}$-aryl or the moiety $N(R^3)2$ is a cyclic amino radical, and radicals of the general formulae (IIIa-e)

$$A\text{---}E \quad (IIIa)$$

$$A\text{---}SO_2\text{---}E \quad (IIIb)$$

$$A\text{---}B\text{---}SO_2R^2 \quad (IIIc)$$

$$A\text{---}SO_3W \quad (IIId)$$

$$A\text{---}COW \quad (IIIe)$$

where A, B, E and $R^2$ are as defined above and W is OH, $NH_2$, or OM, where M can be an alkali metal ion, half an equivalent of an alkaline earth metal ion, an ammonium ion or an organic ammonium ion.

For the purposes of the invention, alkyl or alkylene or alkoxy are each, independently of one another, a straight-chain, cyclic, branched or unbranched alkyl or alkylene or alkoxy radical which may be further substituted by $C_1$–$C_4$-alkoxy radicals. The same applies to the alkyl part of an arylalkyl radical.

In all contexts, $C_1$–$C_6$-alkyl is preferably methyl, ethyl, n-propyl, isopropyl, n-butyl, tert-butyl, n-pentyl, cyclohexyl or n-hexyl, $C_1$–$C_8$-alkyl may also be, for example, n-heptyl, n-octyl or isooctyl, $C_1$–$C_{12}$-alkyl may also be, for example, n-decyl and n-dodecyl and $C_1$–$C_{20}$-alkyl may also be n-hexadecyl and n-octadecyl.

In all contexts, $C_1$–$C_4$-alkylene is preferably methylene, 1,1-ethylene, 1,2-ethylene, 1,1-propylene, 1,2-propylene, 1,3-propylene, 1,1-butylene, 1,2-butylene, 2,3-butylene and 1,4-butylene, $C_1$–$C_8$-alkylene may also be 1,5-pentylene, 1,6-hexylene, 1,1-cyclohexylene, 1,4-cyclohexylene, 1,2-cyclohexylene and 1,8-octylene.

In all contexts, $C_1$–$C_4$-alkoxy is preferably methoxy, ethoxy, isopropoxy, n-propoxy, n-butoxy and tert-butoxy, $C_1$–$C_8$-alkoxy may also be cyclohexyloxy.

The general designation aryl as substituent encompasses carbocyclic radicals and heteroaromatic radicals in which no, one, two or three framework atoms per ring, but at least one framework atom in the overall radical, are heteroatoms selected from the group consisting of nitrogen, sulphur and oxygen. $C_5$–$C_{10}$-aryl is, by way of example and preferably, phenyl, pyridyl, o-, m-, or p-tolyl, $C_5$–$C_{14}$-aryl may also be anthracenyl.

The same applies to the aryl part of an arylalkyl radical. $C_6$–$C_{15}$-arylalkyl is, by way of example and preferably, benzyl.

For the purposes of the invention, haloalkyl and fluoroalkyl are each, independently of one another, a straight-chain, cyclic, branched or unbranched alkyl radical which may be monosubstituted, polysubstituted or fully substituted by halogen atoms selected independently from the group consisting of fluorine, chlorine and bromine or by fluorine.

In all contexts, $C_1$–$C_8$-haloalkyl is, by way of example and preferably, trifluoromethyl, trichloromethyl, 2,2,2-trifluoroethyl, pentafluoroethyl or nonafluorobutyl, $C_1$–$C_8$-fluoroalkyl may be trifluoromethyl, 2,2,2-trifluoroethyl, pentafluoroethyl or nonafluorobutyl.

Protected formyl is a formyl radical which has been protected by conversion into an aminal, acetal or a mixed aminal-acetal, with the aminals, acetals and mixed aminal-acetals being able to be acyclic or cyclic.

Protected formyl is, by way of example and preferably, a 1,1-(2,5-dioxy)cyclopentylene radical.

In the process of the invention, preference is given to using aromatic compounds of the general formula (I) in which n=one and Ar is a substituted or unsubstituted aromatic radical selected from the group consisting of phenyl, naphthyl, biphenyl, binaphthyl, phenanthrenyl, anthracenyl, fluorenyl, pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, triazolyl and quinolinyl which may also be further substituted by no, one, two or three radicals per ring which are selected independently from the group consisting of fluorine, nitro, cyano, di($C_1$–$C_6$-alkyl)amino, formyl, $C_1$–$C_6$-alkyl, $C_5$–$C_{10}$-aryl, $C_1$–$C_8$-fluoroalkyl, $C_1$–$C_8$-fluoroalkoxy, $C_1$–$C_8$-alkoxy, CO($C_1$–$C_4$-alkyl), COO—($C_1$–$C_6$)-alkyl, —CON($C_1$–$C_6$-alkyl)$_2$, and X is chlorine, bromine, iodine, $C_1$–$C_8$-perfluoroalkylsulphonyloxy such as trifluoromethanesulphonyloxy or nonafluorobutanesulphonyloxy or benzenesulphonyloxy or tolylsulphonyloxy.

In the process of the invention, particular preference is given to using aromatic compounds of the general formula (I) in which n=one and Ar is a phenyl radical which may be further substituted by no, one, two or three radicals selected independently from the group consisting of fluorine, cyano, $C_1$–$C_4$-alkyl, formyl, trifluoromethyl, trifluoromethoxy, acetyl, COO—($C_1$–$C_6$)-alkyl, —CON($C_1$–$C_6$-alkyl)$_2$ and X is chlorine or bromine.

Very particular preference is given to using 4-chlorobenzotrifluoride

Palladium catalysts used are, by way of example and preferably, palladium complexes.

Palladium complexes can, for example, be generated from palladium compounds and suitable ligands in the reaction solution, or can be used in the form of previously isolated palladium complexes.

Isolated palladium complexes suitable for the process of the invention are, for example, palladium complexes containing phosphorus compounds such as phosphines, phosphites, phosphonites or mixtures thereof, preferably phosphines, as ligands.

As palladium complexes which can contain phosphorus compounds as ligands, use is made, by way of example and preferably, of complexes of the general formula (IV), $$[PdL_2An_2] \qquad (IV)$$

where

L is in each case a monophosphorus compound or $L_2$ together represents a diphosphorus compound and An is an anion, preferably chloride, bromide, iodide, acetate, propionate, allyl or cyclopentadienyl, or complexes of the general formula (IVb)

$$[PdL_n] \qquad (IVb)$$

where n is 2, 3 or 4 and

L is in each case a monophosphorus compound or can represent half an equivalent of a diphosphorus compound.

Monophosphorus compounds are, by way of example and preferably, compounds of the general formula (Va)

$$P(E-R^4)_3 \qquad (Va)$$

where

E are each, independently of one another and independently of $R^4$, absent or oxygen and the radicals $R^4$ are each, independently of one another, $C_1$–$C_8$-alkyl or unsubstituted phenyl, naphthyl or ferrocenyl or phenyl, naphthyl or ferrocenyl substituted by one, two or three radicals $R^5$, where $R^5$ is $C_1$–$C_8$-alkyl, $C_1$–$C_8$-alkoxy, chlorine, fluorine, N($C_1$–$C_6$-alkyl)$_2$, CO$_2$—($C_1$–$C_6$-alkyl), —CON($C_1$–$C_6$-alkyl)$_2$, cyano or CO($C_1$–$C_6$-alkyl).

Particularly preferred monophosphorus compounds are those of the general formula (Va) in which E is absent and $R^4$ are each, independently of one another, $C_1$–$C_8$-alkyl or unsubstituted phenyl or naphthyl or ferrocenyl or phenyl or naphthyl or ferrocenyl substituted by one, two or three radicals $R^5$, where $R^5$ is $C_1$–$C_8$-alkyl, $C_1$–$C_8$-alkoxy, chlorine or fluorine.

Very particular preference is given to monophosphorus compounds of the general formula (Va) in which E is absent and two or three of the radicals $R^4$ are each, independently of one another, $C_1$–$C_8$-alkyl and no or one radical $R^4$ is unsubstituted phenyl or naphthyl or phenyl or naphthyl substituted by one, two or three radicals $R^5$, where $R^5$ is $C_1$–$C_8$-alkyl, $C_1$–$C_8$-alkoxy, chlorine or fluorine.

Even more preferred monophosphorus compounds are tri(tert-butyl)phosphine, phenyldi(tert-butyl)phosphine and ferrocenyldi(tert-butyl)phosphine.

Diphosphorus compounds can be, by way of example and preferably, compounds of the general formula (Vb), $$(R^6-E)_2P-E-Z-E-P(E-R^6)_2 \qquad (Vb)$$

where

E are each, independently of one another and independently of $R^6$ and Z, absent or oxygen and the radicals $R^6$ are each, independently of one another, $C_1$–$C_8$-alkyl or phenyl, naphthyl or heteroaryl having from 5 to 12 framework carbon atoms which may be unsubstituted or substituted by one, two or three radicals $R^7$, where $R^7$ are selected independently from the group consisting of $C_1$–$C_8$-alkyl, $C_1$–$C_8$-alkoxy, fluorine and cyano and Z is an unsubstituted or substituted radical selected from the group consisting of $C_1$–$C_4$-alkylene, 1,2-phenylene, 1,3-phenylene, 1,2-cyclohexyl, 1,1'-ferrocenyl, 1,2-ferrocenyl, 2,2'-(1,1'-binaphthyl) and 1,1'-biphenyl.

Preference is given to using complexes which contain monophosphorus compounds as ligands.

Preferred isolated palladium complexes are bistriphenylphosphinepalladium(II) dichloride, tetrakistriphenylphosphinepalladium(0), bistri-o-tolylphosphinepalladium(0), tricyclohexylphosphinepalladium(0)-diallyl ether complex, bistricyclohexylphosphinepalladium(0).

In the process of the invention, palladium complexes generated in the reaction solution from palladium compounds and ligands are preferred as palladium catalysts.

As palladium compounds, it is possible to use, by way of example and preferably, $Pd_2$(dibenzylideneacetone)$_3$ or allylpalladium chloride or bromide or compounds of the general formula (VIa), $$Pd(Y^1)_2 \qquad (VIa)$$

where $y^1$ is an anion, preferably chloride, bromide, acetate, propionate, nitrate, methanesulphonate, trifluoromethanesulphonate, acetylacetonate, allyl or cyclopentadienyl, or palladium compounds of the general formula (VIb)

$$Pd(Y^2)_2L_2 \qquad (VIb)$$

where $y^2$ is an anion, preferably chloride, bromide, acetate, methanesulphonate or trifluoromethanesulphonate, nonafluorobutanesulphonate, tetrafluoroborate or hexafluorophosphate and L are each a nitrile, preferably acetonitrile, benzonitrile or benzyl nitrile, or an olefin, preferably cyclohexene or cyclooctene, or $L_2$ together represents a diolefin, preferably norbornadiene or 1,5-cyclooctadiene, or palladium compounds of the general formula (VIc)

$$M_2[Pd(Y^3)_4] \qquad (VIc),$$

where $Y^3$ is a halide, preferably chloride or bromide, and

M is lithium, sodium, potassium, ammonium or organic ammonium.

Preferred palladium compounds are palladium(II) acetate, palladium(II) chloride, palladium(II) bromide, palladium(II) propionate, palladium(II) acetylacetonate, lithium, sodium or potassium tetrachloropalladate, bisbenzonitrilepalladium (II) chloride, bisacetonitrilepalladium(II) chloride, cyclopentadienyl(allyl)palladium(II), and palladiumdibenzylideneacetone complexes such as [$Pd_2$(dba)$_3$].

Preference is given to using the phosphorus compounds of the general formulae (Va) and (Vb) as ligands for the generation of palladium complexes in the reaction solution, with monophosphorus compounds of the general formula (Va) being particularly preferred. The above-mentioned preferred ranges apply in the same way.

The molar ratio of phosphorus to palladium in the reaction mixture can be, for example, from 1:1 to 100:1, preferably from 2:1 to 15:1, particularly preferably from 2:1 to 10:1.

In the process of the invention, the molar ratio of X to be replaced in compounds of the general formula (I) to palladium can be, for example, from 10 to 20 000; preference is given to a ratio of from 100 to 5 000, very particularly preferably from 500 to 2 000.

The process of the invention is carried out in the presence of at least one, preferably one, bulky nitrogen base.

Bulky nitrogen bases are, for example, amines of the general formula $$NR^8R^9R^{10} \qquad (VII)$$

where $R^8$, $R^9$ and $R^{10}$ are each, independently of one another, $C_1$–$C_{20}$-alkyl, $C_5$–$C_{14}$-aryl or $C_6$–$C_{15}$-arylalkyl or two or three of the radicals $R^8$, $R^9$ and $R^{10}$ together with the nitrogen atom may form a monocyclic, bicyclic or tricyclic heterocycle having from 4 to 8 carbon atoms per ring, with the proviso that one, two or three of the radicals $R^8$, $R^9$ and $R^{10}$, preferably two or three, are each, independently of one another, either bound to the nitrogen atom via a tertiary or quaternary $Sp^3$ carbon atom or are an aryl radical which is monosubstituted or disubstituted, preferably disubstituted, in the ortho positions.

Radicals which may be bound to the nitrogen atom via a tertiary or quaternary $Sp^3$ carbon atom are, by way of example and preferably, isopropyl, isobutyl, tert-butyl, 1-methylbutyl, 1-ethylpropyl, 1,1-dimethylpropyl, 1,2-dimethylpropyl, 1-methylpentyl, 1,1-dimethylbutyl, 1,2-dimethylbutyl, 1,3-dimethylbutyl, 1-ethylbutyl, 1,1,2-trimethylpropyl, 1,2,2-trimethylpropyl, 1-ethyl-1-methylpropyl, cyclopentyl, cyclohexyl and cycloheptyl.

Aryl radicals which are monosubstituted or disubstituted in the ortho positions are, for example, o-tolyl, 2,6-dimethylphenyl, 2-ethyl-6-methylphenyl, 2,6-diisopropylphenyl, o-anisyl and 2,6-dimethoxyphenyl.

For the purposes of the invention, monocyclic heterocycles are, for example, N-methyl-2,2,6,6-tetramethylpiperidine and N-methyl-2,5-dimethylpyrrolidine.

Further bulky nitrogen bases are N-heteroaromatic compounds which are substituted in both the ortho positions relative to the nitrogen.

These are preferably 2,6-disubstituted pyridines such as 2,6-lutidine, 2,6-diethylpyridine, 2,6-diisopropylpyridine, 2,6-dimethoxypyridine, 2,6-di-tert-butylpyridine.

In the process of the invention, bulky nitrogen bases used are very particularly preferably ethyldiisopropylamine, triisopropylamine, diisopropylaniline, triisobutylamine, ethyldiisobutylamine, dicyclohexylmethylamine, dicyclohexylethylamine, cyclohexyldiethylamine, cyclohexyldimethylamine and 2,6-bis-diisopropylpyridine, among which dicyclohexylmethylamine, dicyclohexylethylamine, cyclohexyldimethylamine, cyclohexyldimethylamine are very particularly preferred.

The molar amount of base used can be, for example, from 0.5 to 100 times, preferably from 1.0 to 10 times, particularly preferably from 1.0 to 1.5 times and very particularly preferably from 1.0 to 1.2 times, the molar amount of X to be replaced in the general formula (I).

In an embodiment of the process of the invention, the bulky nitrogen base can be used in combination with another base. In this case, for example, from 1 to 95% of the amount of bulky nitrogen base can be replaced by a nonbulky nitrogen base.

Nonbulky nitrogen bases for the purposes of the invention are, for example, alkali metal and alkaline earth metal carboxylates such as acetates, propionates, benzoates, alkali metal and alkaline earth metal carbonates, hydrogencarbonates, phosphates, hydrogenphosphates, hydroxides. Alkali metals are preferably lithium, sodium, potassium and caesium, alkaline earth metals are preferably calcium, magnesium and barium.

As olefins which bear at least one hydrogen atom on the double bond, it is possible to use, for example, those of the general formula (VIII), $$R^{11}CH=C^{12}R^{13} \qquad (VII)$$

where, independently of one another, $R^{11}$ is hydrogen or methyl and $R^{12}$ is hydrogen or methyl and $R^{13}$ can be hydrogen, cyano, $SO_3M$, $C_1$–$C_8$-alkyl, a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the total molecule, may be replaced by heteroatoms selected from the group consisting of nitrogen, sulphur and oxygen or a radical of the general formula (IX)

(IX)

where

G is OM, OH, $NH_2$, $OR^{14}$, $NHR^{14}$ or $N(R^{14})_2$, and $R^{14}$ is $C_1$–$C_{12}$-alkyl, $C_6$–$C_{15}$-arylalkyl or $C_5$–$C_{14}$-aryl or the $N(R^{14})_2$ moiety is a cyclic amino radical such as morpholino, pyrrolidino or piperidino, and M can be an alkali metal ion, half an equivalent of an alkaline earth metal ion, an ammonium ion or an organic ammonium ion.

The carbocyclic aromatic radicals and heteroaromatic radicals can be substituted in the same way as described under the aromatic compounds of the general formula (I).

Preferred examples of olefins of the general formula (X) are ethene, propene, butene, 1,1,1-trifluoro-2-propene, substituted or unsubstituted vinyl-$C_6$–$C_{10}$-aromatics such as styrene or the isomeric vinylnaphthalenes, 2-, 3- or 4-fluorostyrene, 2-, 3- or 4-chlorostyrene, 2-, 3- or 4-bromostyrene, 2-, 3- or 4-iodostyrene, 2-, 3- or 4-cyanostyrene, 2-, 3- or 4-($C_1$–$C_{12}$)-alkoxystyrene such as 2-, 3- or 4-methoxystyrene, 2-, 3- or 4-nitrostyrene, 2-, 3- or 4-styrenecarboxylic acid, $C_1$–$C_{12}$-alkyl 2-, 3- or 4-styrenecarboxylates such as methyl 2-, 3- or 4-styrenecarboxylate, $C_6$–$C_{12}$-aryl 2-, 3- or 4-styrenecarboxylates such as phenyl 2-, 3- or 4-styrenecarboxylate, 2-, 3- or 4-styrenesulphonic acid or their salts, 3- or 4-vinylphthalic acid, di-$C_1$–$C_{12}$-alkyl 3- or 4-vinylphthalates such as dimethyl 3- or 4-vinylphthalate, di-$C_6$–$C_{10}$-aryl 3- or 4-vinylphthalates such as diphenyl 3- or 4-vinylphthalate, 3- or 4-vinylphthalic anhydride, vinylhetaryls such as N-vinylimidazole or 2- or 4-vinylpyridine, also acrylonitrile, acrylic acid, $C_1$–$C_{12}$-alkyl acrylates such as methyl acrylate, ethyl acrylate, n-propyl acrylate, 2-ethylhexyl acrylate, acrylamide, vinylsulphonic acid and its sulphonates and acrylamide.

As olefins having at least one hydrogen substituent, very particular preference is given to ethylene, propene, acrylonitrile, acrylic acid, methyl acrylate, 2-ethylhexyl acrylate, acrylamide, 1,1,1-trifluoro-2-propene and styrene, with especial preference being given to acrylonitrile, methyl acrylate, acrylamide and styrene and greatest preference being given to acrylamide.

The amount of olefin used can be, for example, from 0.2 to 200 times (when used as solvent) the molar amount of the aromatic compound of the general formula (I); from 0.5 to 5 times is preferred and from 0.8 to 1.2 times is very particularly preferred. Even greater preference is given to 0.9 to 1.0 times.

If aromatic compounds of the general formula (I) or olefins of the general formula (VIII) which bear a free acid group such as a sulphonic acid or carboxylic acid group, the amount of base used, viz. a bulky nitrogen base or nonbulky nitrogen base, has to be increased correspondingly.

The process of the invention is carried out in the presence of a dipolar aprotic solvent.

Preferred dipolar aprotic solvents are amide solvents such as dimethylformamide, dimethylacetamide, N-methylpyrrolidone or N-methylcaprolactam;

sulphoxides and sulphones such as dimethyl sulphoxide or tetramethylene sulphone (sulpholane) or mixtures of such solvents;

nitriles such as acetonitrile, benzonitrile and benzyl nitrile, ketones such as dimethyl ketone, diethyl ketone, methyl tert-butyl ketone.

Dimethylformamide, dimethylacetamide and N-methylpyrrolidone are particularly preferred.

Dimethylacetamide is very particularly preferred.

The amount of any solvent used can be, for example, from 50 ml to 5000 ml, preferably from 100 to 500 ml, per mol of the aromatic compound of the general formula (I).

The reaction temperature can be, for example, from 20° C. to 200° C., preferably from 80 to 150° C. and particularly preferably from 0° C. to 120° C.

The reaction can be carried out at, for example, from 0.2 to 100 bar; preference is given to atmospheric pressure.

The reaction time can be, for example, from 0.2 hour to 72 hours; preference is given to from 1 to 36 hours.

The reaction is preferably carried out under a protective gas atmosphere with substantial exclusion of oxygen and moisture. Possible protected gases are, for example, nitrogen and noble gases such as argon or mixtures of such gases.

In a preferred embodiment of the process of the invention, the aromatic compound of the general formula (I) together with the olefin, the base, the palladium compound and the ligand are placed in a reaction vessel under protective gas and the mixture is heated to the reaction temperature while stirring. After the reaction is complete, the mixture is poured into water. Solid products then precipitate and can be filtered off with suction and, for example, washed with water. Liquid products can be extracted by means of an organic solvent which is immiscible or sparingly miscible with water and be worked up, for example, by distillation.

Solid products can, if appropriate, be purified further by, for example, recrystallization or reprecipitation.

As an alternative, it is also possible for the aromatic compound of the general formula (I) together with the olefin, the base and the ligand to be placed in a reaction vessel and the palladium compound to be added.

Furthermore, it is also possible for the aromatic compound of the general formula (I) together with the base, the ligand and the palladium compound to be placed in a reaction vessel and the olefin to be added.

Furthermore, it is also possible for the olefin together with the base, the ligand and the palladium compound to be placed in a reaction vessel and the aromatic compound of the general formula (I) to be added.

Furthermore, it is also possible for the base, the ligand and the aromatic compound of the general formula (I) to be placed in a reaction vessel and the palladium compound to be added.

In each of the possible methods of addition mentioned above, the ligand can also be added together with the palladium compound.

It is advantageous to use a weakly acidic aqueous solution during the work-up to bind any remaining base as salt. The base can, for example, be recovered by alkalisation and extraction of the washing liquid with an organic solvent.

The process of the invention gives arylolefins of the general formula (X)

$$Ar-(R^{11}C=CR^{12}R^{13})_n \quad (X)$$

where

Ar and n are as defined under the general formula (I) and $R^{11}$, $R^{12}$, $R^{13}$ are as defined under the general formula (VIII).

The process of the invention is particularly useful for preparing arylacrylic acid derivatives of the general formula (XI)

$$Ar-(R^{11}=R^{12}R^{13}) \quad (XI)$$

where

Ar is as defined under the general formula (I) and $R^{11}$, $R^{12}$ are as defined under the general formula (X) and $R^{13}$ is cyano or a radical of the general formula (XI) with the meanings specified there.

The advantages of the process of the invention are the ease with which it can be carried out and the high yields of aromatic olefins. Furthermore, high catalyst turnover numbers (TONs) of far above 100 mol of haloaromatic/mol of palladium catalyst are achieved.

The invention is further illustrated but is not intended to be limited by the following examples in which all parts and percentages are by weight unless otherwise specified.

EXAMPLES

Examples 1–9

0.4 ml of 4-chlorobenzotrifluoride, 0.178 g of acrylamide, 1.4 mg (0.24 mol %) of palladium acetate and 4.8 mg of phenyldi(t-butyl)-phosphine and 2 ml of dimethylacetamide are placed in a Schlenk vessel. The indicated amount of the specified base is in each case added to this initial charge and the mixture is heated to 130° C. under protective gas. After 4 hours, samples are taken and analysed by HPLC.

| Example number | Base | Weight used [g] | Yield [%] |
|---|---|---|---|
| 1 (comparison) | Na₂CO₃ | 0.382 | 0 |
| 2 (comparison) | Triethylamine | 0.364 | 6.4 |
| 3 (comparison) | Diazabicyclooctane | 0.404 | 15.4 |
| 4 (comparison) | Diazabicycloundecane | 0.548 | 0 |
| 5 | Ethyldiisopropylamine | 0.465 | 35.4 |
| 6 | Dicyclohexylmethylamine | 0.703 | >99 |
| 7 | Dicyclohexylethylamine | 0.754 | 83 |
| 8 | Cyclohexyldiethylamine | 0.559 | >99 |
| 9 | Cyclohexyldimethylamine | 0.458 | >99 |

Example 10

0.40 ml of 4-chlorobenzotrifluoride, 0.178 g of acrylamide, 0.7 mg of palladium acetate (0.12 mol %), 2.7 mg of di(tert-butyl)phenylphosphine and 3 ml of dimethylacetamide are placed in a Schlenk vessel. 0.559 g of cyclohexyldiethylamine is added to this initial charge, and the mixture is then heated to 120° C. under protective gas. After 5.5 hours, a sample is taken and analysed by HPLC. 84% conversion to the desired product (TON=700, TOF= 127 h⁻¹).

Examples 11 and 12

In each case in a Schlenk vessel, 237.6 mg of acrylamide, 0.50 ml of 4-chlorobenzotrifluoride, 0.87 ml of dicyclohexylmethylamine, 4.2 mg of palladium acetate, 16.5 mg of di(tert-butyl)phenylphosphine and 100 mg of 1,3,5-trimethoxybenzene as internal standard are dissolved once in 3 ml of dimethylacetamide (Example 11) and once in 3 ml of dioxane (Example 12). The vessels are then placed in the same oil bath at 100° C. and samples for HPLC are taken at regular intervals. The results were used to produce a time-conversion table.

| Time [h] | Conversion in % (Example 11) | Conversion in % (Example 12) |
|---|---|---|
| 0 | 0 | 0 |
| 0.5 | 1.3 | 2.3 |
| 1 | 8.3 | 3.7 |
| 1.5 | 11.4 | 5.8 |
| 2 | 15.2 | 8.4 |
| 2.5 | 20.2 | 8.4 |
| 4 | 30.1 | 14.5 |

Time-conversion table comparing the solvents dimethylacetamide (Example 11) and 1,4-dioxane (Example 12).

Examples 13 and 14

In each case in a Schlenk vessel, 237.6 mg of acrylamide, 0.50 ml (3.71 mmol) of 4-chlorobenzotrifluoride, 0.87 ml of dicyclohexylmethylamine, 0.8 mg (0.11 mol %) of palladium acetate, 3.3 mg of di(tert-butyl)phenylphosphine and 100 mg of 1,3,5-trimethoxybenzene as internal standard are dissolved once in 4 ml of dimethylacetamide (Example 13) and once in 4 ml of dioxane (Example 14). Both tubes are then placed in the same oil bath at 130° C. (the mixture containing dioxane in a pressure tube) and stirred for 3 hours. A sample is taken in each case before the reaction and after the end of the reaction and the conversion is calculated from HPLC analysis of the samples. In dimethylacetamide (Example 13), 33% conversion (TON=298, TOF=99 h⁻¹) was achieved after 3 hours, while in dioxane (Example 14), the conversion was only 2.4%.

Examples 15 and 16

In each case in a Schlenk vessel, 237.6 mg (3.34 mmol) of acrylamide, 0.50 ml (3.71 mmol) of 4-chlorobenzotrifluoride, 0.87 ml (4.08 mmol) of dicyclohexylmethylamine, 0.8 mg (3.7 µmol) of palladium acetate, 3.0 mg (14.9 µmol) of tri(tert-butyl)phosphine and 100 mg of 1,3,5-trimethoxybenzene as internal standard are dissolved once in 4 ml of dimethylacetamide (Example 15) and once in 4 ml of dioxane (Example 16). Both tubes are then placed in the same oil bath at 130° C. (the mixture containing dioxane in a pressure tube) and stirred for 3 hours. A sample is taken in each case before the reaction and after the end of the reaction and the conversion is calculated from HPLC analysis of the samples. In dimethylacetamide (Example 15), 52% conversion (TON=469, TOF=156 h⁻¹) was achieved after 3 hours, while in dioxane (Example 16), there was no conversion.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing arylolefins, comprising reacting aromatic compounds of the general formula (I), $$Ar\text{—}[X]_n \qquad (I),$$

where
n is one or two and
Ar is a substituted or unsubstituted aromatic radical and
X are each, independently of one another, chlorine, bromine, iodine or a sulphonate,
with olefins which bear at least one hydrogen atom on the double bond
in the presence of a palladium catalyst,
at least one bulky nitrogen base and
in the presence of a dipolar aprotic solvent,
wherein the bulky nitrogen bases used are amines of the general formula, $$NR^8R^9R^{10} \qquad (VII)$$

where
$R^8$, $R^9$ and $R^{10}$ are each, independently of one another, $C_1$–$C_{20}$-alkyl, $C_5$–$C_{14}$-aryl or $C_6$–$C_{15}$-arylalkyl or two or three of the radicals $R^8$, $R^9$ and $R^{10}$ together with the nitrogen atom may form a monocyclic, bicyclic or tricyclic heterocycle having from 4 to 8 carbon atoms per ring,
with the proviso that one, two or three of the radicals $R^8$, $R^9$ and $R^{10}$, are each, independently of one another, either bound to the nitrogen atom via a tertiary or quaternary sp$^3$ carbon atom or are an aryl radical which is monosubstituted or disubstituted, in the ortho positions or
N-heteroaromatic compounds which are substituted in the two ortho positions relative to the nitrogen.

2. Process according to claim 1, wherein the dipolar aprotic solvents used are amide solvents, sulphoxides, nitriles, ketones or sulpholanes or mixtures thereof.

3. Process according to claim 1, wherein the dipolar aprotic solvents used are dimethylformamide, dimethylacetamide, N-methylpyrrolidone or mixtures thereof.

4. Process according to claim 1, wherein the general formula (I),
Ar is a carbocyclic aromatic radical having from 6 to 24 framework carbon atoms or a heteroaromatic radical having from 5 to 24 framework carbon atoms in which no, one, two or three framework carbon atoms per ring, but at least one framework carbon atom in the total molecule, is/are replaced by heteroatoms selected from the group consisting of nitrogen, sulphur and oxygen, where
the carbocyclic aromatic radical or heteroaromatic radical is substituted by up to five identical or different substituents per ring selected from the group consisting of hydroxy, fluoro, nitro, cyano, free or protected formyl, $C_1$–$C_{12}$-alkyl, $C_5$–$C_{14}$-aryl, $C_6$–$C_{15}$-arylalkyl, —PO—[($C_1$–$C_8$)-alkyl]$_2$, —PO—[($C_5$–$C_{14}$)-aryl]$_2$, —PO—[($C_1$–$C_8$)-alkyl)($C_5$–$C_{14}$)-aryl)], tri($C_1$–$C_8$-alkyl)siloxyl and radicals of the general formula (II), $$A\text{—}B\text{—}D\text{—}E \qquad (II)$$

where, independently of one another,
A is absent or is a $C_1$–$C_8$-alkylene radical and
B is absent or is oxygen, sulphur or $NR^1$,
where $R^1$ is hydrogen, $C_1$–$C_8$-alkyl, $C_6$–$C_{15}$-arylalkyl or $C_5$–$C_{14}$-aryl and D is a carbonyl group and
E is $R^2$, $OR^2$, $NHR^3$ or $N(R^3)_2$,
where $R^2$ is $C_1$–$C_8$-alkyl, $C_6$–$C_{15}$-arylalkyl, $C_1$–$C_8$-haloalkyl or $C_5$–$C_{14}$-aryl and
$R^3$ are each, independently of one another, $C_1$–$C_8$-alkyl, $C_6$–$C_{15}$-arylalkyl or $C_6$–$C_{14}$-aryl or the moiety $N(R^3)_2$ is a cyclic amino radical,
and radicals of the general formulae (IIIa–e)

$$A\text{—}E \qquad (IIIa)$$

$$A\text{—}SO_2\text{—}E \qquad (IIIb)$$

$$A\text{—}B\text{—}SO_2R^2 \qquad (IIIc)$$

$$A\text{—}SO_3W \qquad (IIId)$$

$$A\text{—}COW \qquad (IIIe)$$

where A, B, E and $R^2$ are as defined above and W is OH, NH$_2$, or OM, where M is an alkali metal ion, half an equivalent of an alkaline earth metal ion, an
ammonium ion or an organic ammonium ion and
X is chlorine, bromine, iodine, trifluoromethanesulphonyloxy or nonafluorobutanesulphonyloxy.

5. Process according to claim 1, wherein the palladium catalysts used are palladium complexes.

6. Process according to claim 1, wherein the palladium catalysts used are palladium complexes which are generated in the reaction solution from palladium compounds and phosphorus compounds.

7. Process according to claim 6, wherein the phosphorus compounds used are monophosphorus compounds of the general formula (Va), $$P(E\text{—}R4)_3 \qquad (Va)$$

where
E are each, independently of one another and independently of R4, absent or oxygen and
the radicals R4 are each, independently of one another, $C_1$–$C_8$-alkyl or unsubstituted phenyl, naphthyl or ferrocenyl or phenyl, naphthyl or ferrocenyl substituted by one, two or three radicals R5, where
R5 is $C_1$–$C_8$-alkyl, $C_1$–$C_8$-alkoxy, chlorine, fluorine, N($C_1$–$C_8$-alkyl)$_2$, $CO_2$—($C_1$–$C_6$-alkyl), —CON($C_1$–$C_6$-alkyl)$_2$, cyano or CO($C_1$–$C_6$-alkyl) or
diphosphorus compounds of the general formula (Vb), $$(R6\text{—}E)_2P\text{—}E\text{—}Z\text{—}E\text{—}P(E\text{—}R6)_2 \qquad (Vb)$$

where
E are each, independently of one another and independently of R6 and Z, absent or oxygen and
the radicals R6 are each, independently of one another, $C_1$–$C_8$-alkyl or phenyl, naphthyl or heteroaryl having from 5 to 12 framework carbon atoms which may be unsubstituted or substituted by one, two or three radicals R7, where
R7 are selected independently from the group consisting of $C_1$–$C_8$-alkyl, $C_1$–$C_8$-alkoxy, fluorine and cyano and
Z is an unsubstituted or substituted radical selected from the group consisting of $C_1$–$C_4$-alkylene, 1,2-phenylene, 1,3-phenylene, 1,2-cyclohexylene, 1,1'-ferrocenylene, 1,2-ferrocenylene, 2,2'-(1,1'-binaphthylene) and 1,1'-biphenylene.

8. Process according to claim 6, wherein the phosphorus compounds used are tri(tert-butyl)phosphine, phenyldi(tert-butyl)phosphine and ferrocenyldi(tert-butyl)phosphine.

9. Process according to claim 6, wherein the molar ratio of phosphorus to palladium in the reaction mixture is from 1:1 to 100:1.

10. Process according to claim 1, wherein the molar ratio of X in compounds of the general formula (I) to palladium is from 10 to 20 000.

11. Process according to claim 1, wherein the bulky nitrogen bases used are dicyclohexylmethylamine, dicyclohexylethylamine, cyclohexyldiethylamine and cyclohexyldimethylamine.

12. Process according to claim 1, wherein the olefins bearing at least one hydrogen atom on the double bond are olefins of the general formula (X), $$R^{11}CH=CR^{12}R^{13} \qquad (X)$$

where, independently of one another, $R^{11}$ is hydrogen or methyl and $R^{12}$ is hydrogen or methyl and $R^{13}$ is hydrogen, cyano, $SO_3M$, $C_1$–$C_8$-alkyl, a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the total molecule, may be replaced by heteroatoms selected from the group consisting of nitrogen, sulphur and oxygen or a radical of the general formula (XI)

(XI)

where

G is one of OM, OH, $NH_2$, $OR^{14}$, $NHR^{14}$ and $N(R^{14})_2$, and $R^{14}$ is $C_1$–$C_{12}$-alkyl, $C_6$–$C_{15}$-arylalkyl or $C_6$–$C_{10}$-aryl or the $N(R^{14})_2$ and M is an alkali metal ion, half an equivalent of an alkaline earth metal ion, an ammonium ion or an organic ammonium ion is a cyclic amino radical.

13. Process according to claim 1, wherein the reaction temperature is from 20° C. to 200° C.

* * * * *